(12) United States Patent
Putten et al.

(10) Patent No.: US 7,081,356 B2
(45) Date of Patent: Jul. 25, 2006

(54) METHOD FOR PRODUCING γ-LINOLENIC ACIDS FROM A CILIATE CULTURE BY ADDING SUITABLE PRECURSOR MOLECULES TO SAID CULTURE MEDIUM

(75) Inventors: Anton van V. Putten, The Hague (NL); Tanja König, Erlangen (DE); Dirk Fabritius, Mainz (DE); Thomas Kiy, Frankfurt (DE); Alexander Leske, Frankfurt (DE); Joem Plote, Hofheim/Ts. (DE)

(73) Assignee: Nutrinova Nutrition Specialities & Food Ingredients GmbH (DE)

( * ) Notice: Subject to any disclaimer, the term of this patent is extended or adjusted under 35 U.S.C. 154(b) by 0 days.

(21) Appl. No.: 10/468,259

(22) PCT Filed: Feb. 8, 2002

(86) PCT No.: PCT/EP02/01302

§ 371 (c)(1),
(2), (4) Date: May 13, 2004

(87) PCT Pub. No.: WO02/064807

PCT Pub. Date: Aug. 22, 2002

(65) Prior Publication Data

US 2004/0180414 A1    Sep. 16, 2004

(30) Foreign Application Priority Data

Feb. 12, 2001 (DE) .................. 101 06 660

(51) Int. Cl.
*C12P 7/64* (2006.01)
(52) U.S. Cl. ...................................... 435/134
(58) Field of Classification Search ................ 435/135, 435/134
See application file for complete search history.

(56) References Cited

U.S. PATENT DOCUMENTS 6,403,345 B1 *   6/2002   Kiy et al. .................. 435/134
6,716,617 B1 *   4/2004   Kiy ........................ 435/258.1

FOREIGN PATENT DOCUMENTS

EP       0 252 716      1/1988
WO       WO-86/03518    6/1986

OTHER PUBLICATIONS

Koroly, M. J. et al., "Unsaturated fatty acid biosynthesis in Tetrahymena. Evidence for two pathways", Chemical Abs. Service DN 86:52528, XP-002218552 & J. Biol. Chem 251(23):7588-7592 (1976).

Nowaza, Y. et al., "Modifications of Membrane Lipid Composition Following the Nutritional Shift-Up of Starved Cells. A Comparison with Membrane Biogenesis in Tetrahymena-Pyriformis", Biochimica et Biophysica Acta 603(2):347-365, XP-002218553 (1980).

* cited by examiner

*Primary Examiner*—Herbert J. Lilling
(74) *Attorney, Agent, or Firm*—Connolly Bove Lodge & Hutz LLP

(57) ABSTRACT

The intention relates to a method for the fermentative production of lipids/fatty acids having high concentrations of omega-6 fatty acids (PUFA, polyunsaturated fatty acids), especially γ-linolenic acids (GLA) in ciliates. Said lipids/fatty acids can be used in human/animal food, and in the pharmaceutical field.

14 Claims, 11 Drawing Sheets

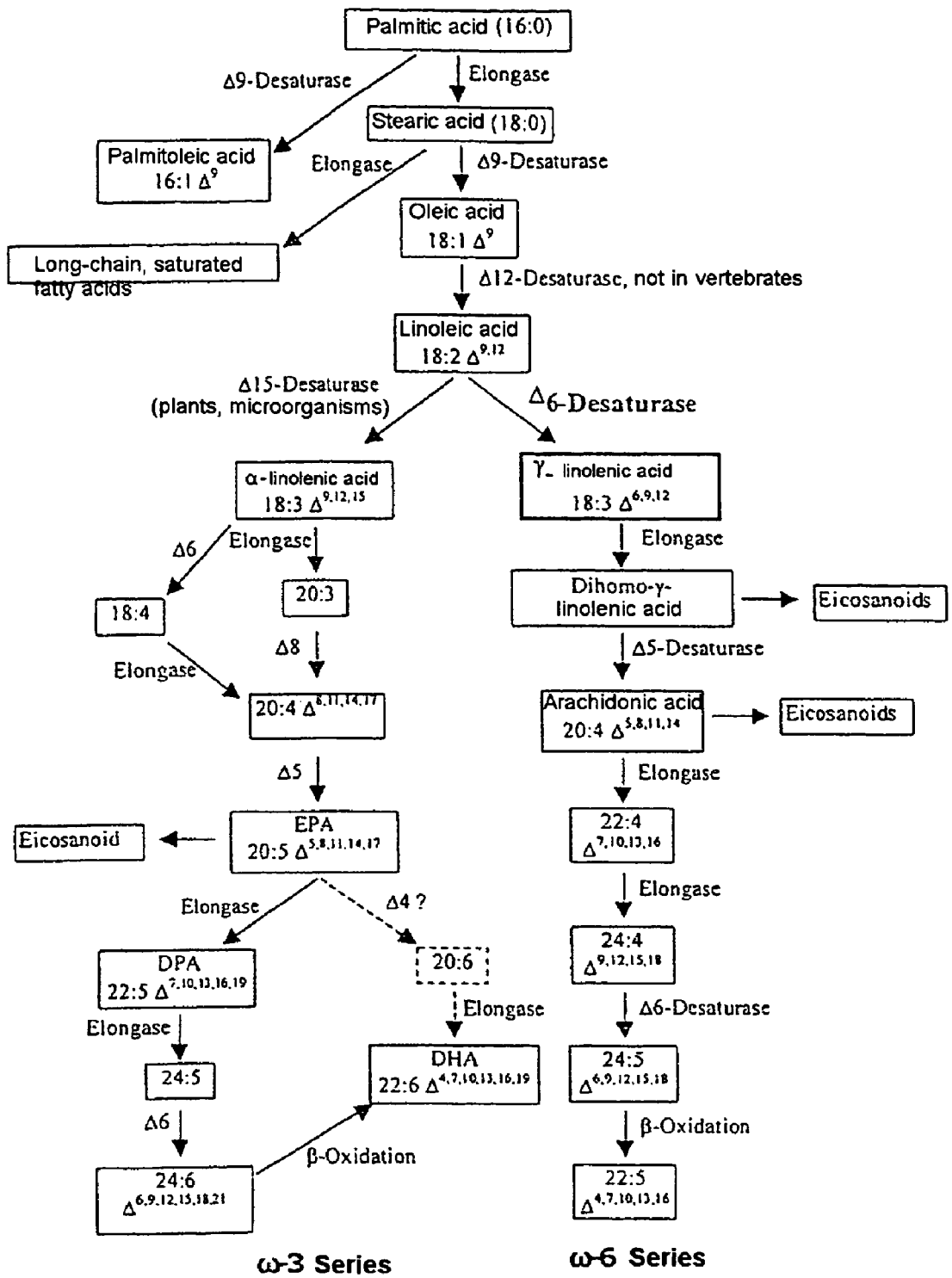
Figure 1 General pathway of PUFA biosynthesis in eukaryotes

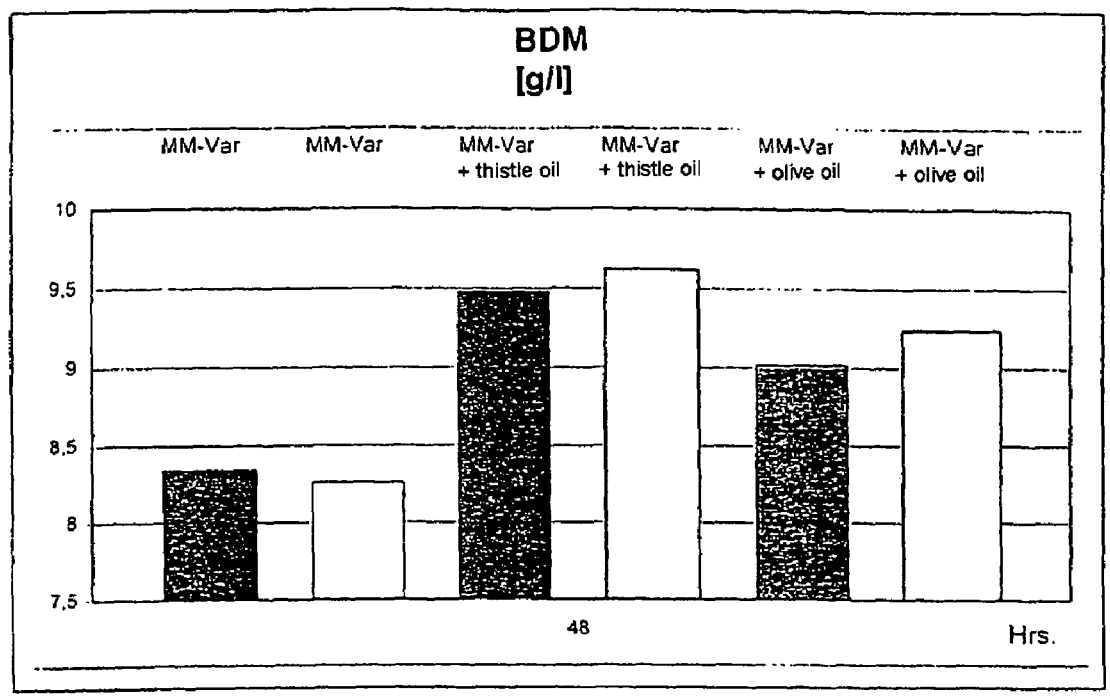
Figure 2  Biomass dry matter achieved in g/l using MM-Var (standard medium), MM-Var + thistle oil and MM-Var + olive oil (two parallel trials each)

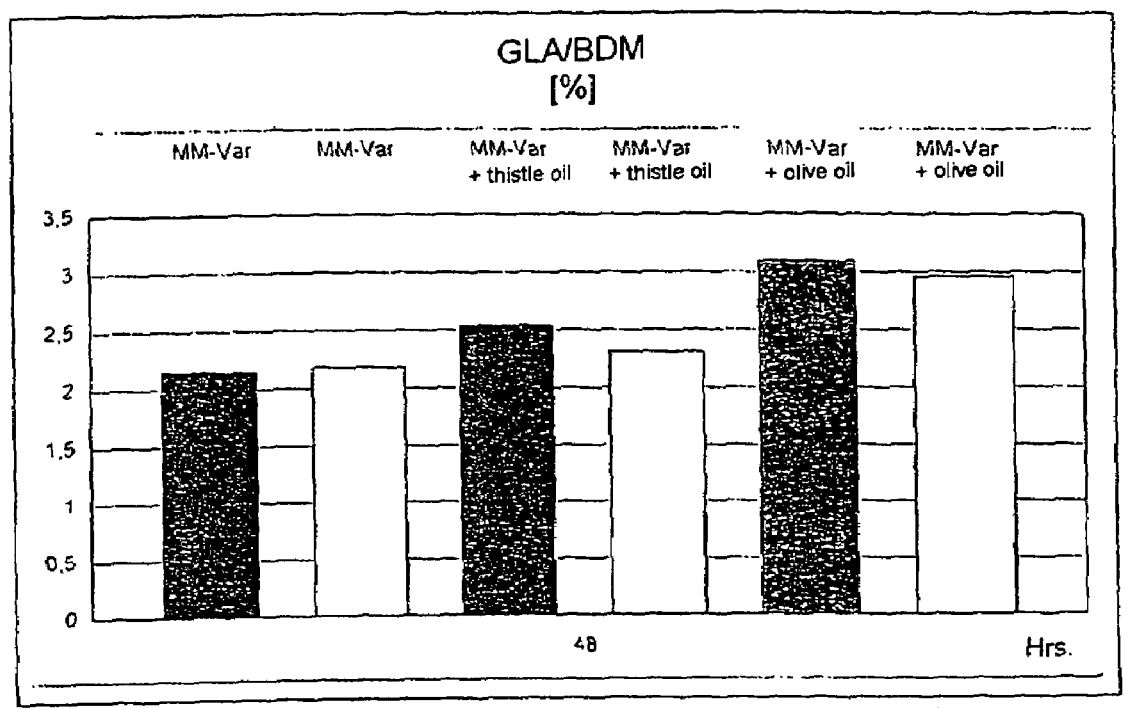
Figure 3  Percent GLA by weight achieved based on biomass dry matter in %, using MM-Var (standard medium), MM-Var + thistle oil and MM-Var + olive oil (two parallel trials each)

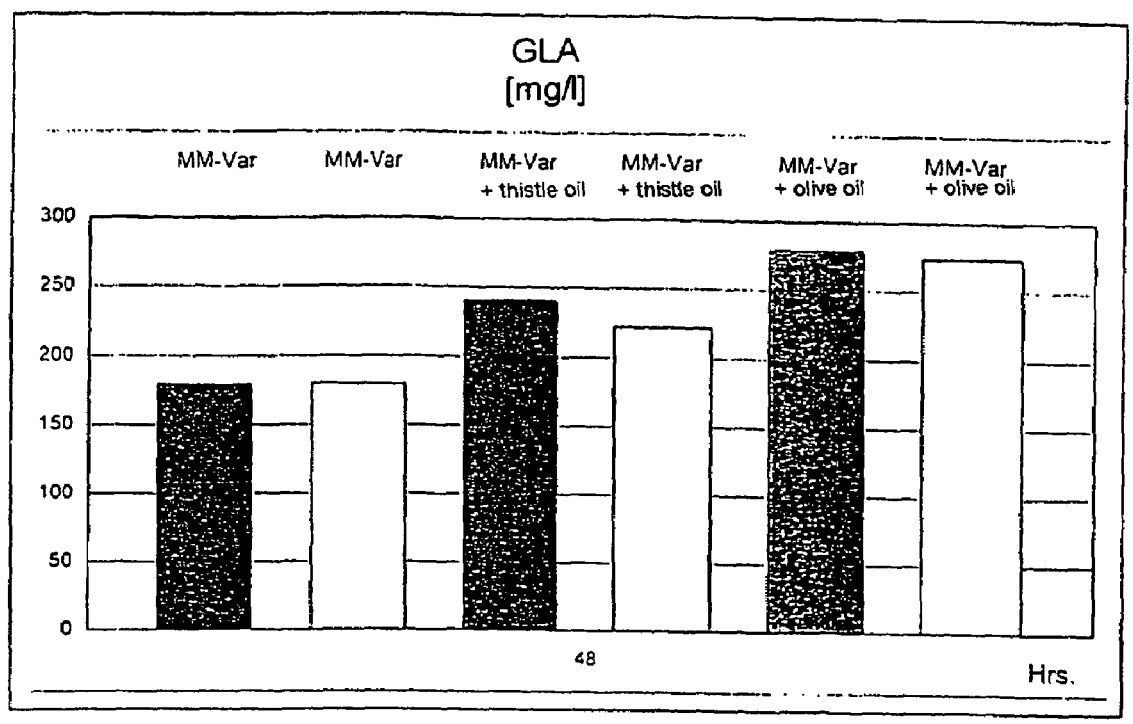
Figure 4 GLA yield achieved in mg/l, using MM-Var (standard medium), MM-Var + thistle oil and MM-Var + olive oil (two parallel trials each)

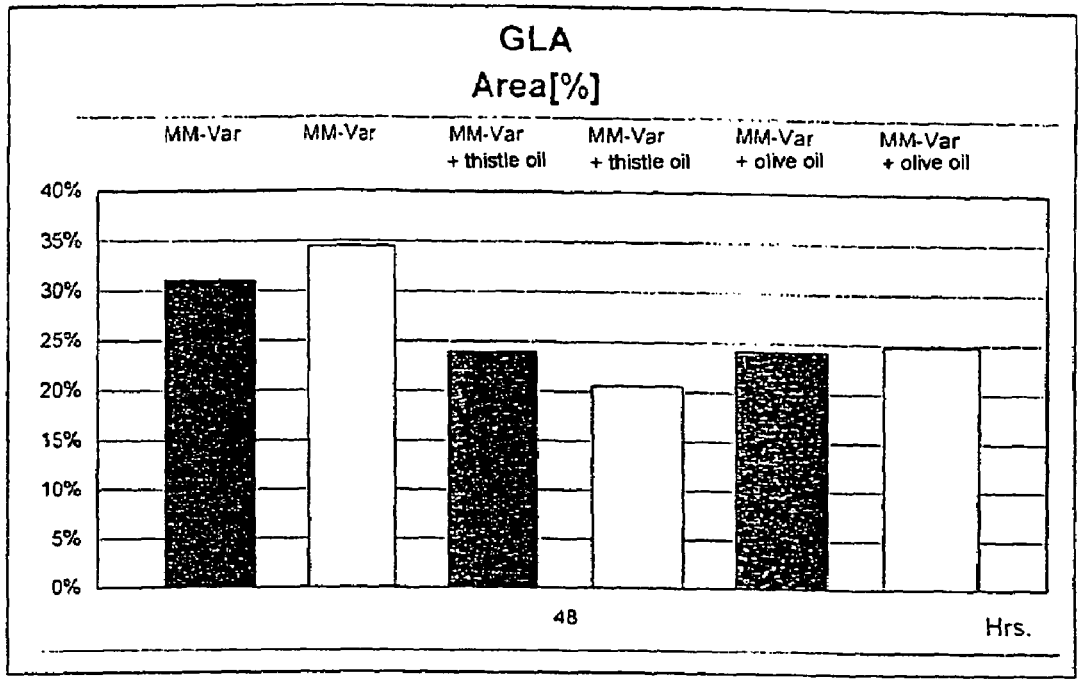
Figure 5  GLA yield achieved in area[%], in g/l, using MM-Var (standard medium), MM-Var + thistle oil and MM-Var + olive oil (two parallel trials each). The area[%] show the proportion of GLA in total lipid content.
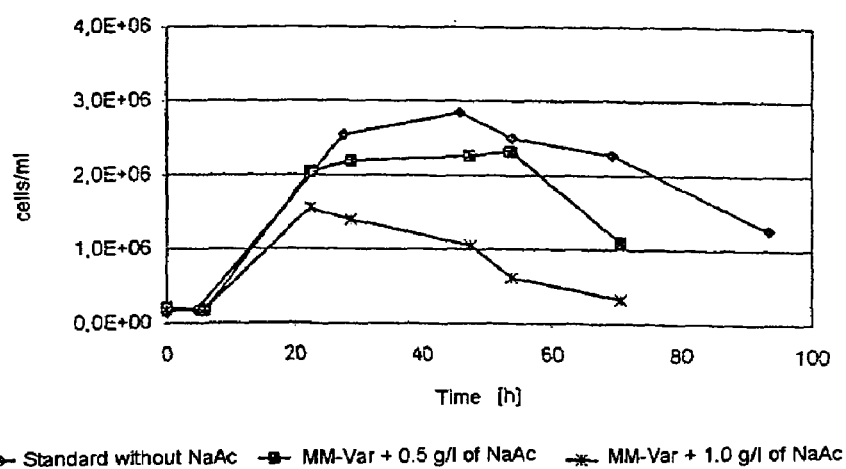
Figure 6  Course of the cell count on addition of NaAc to MM-VAR basal medium

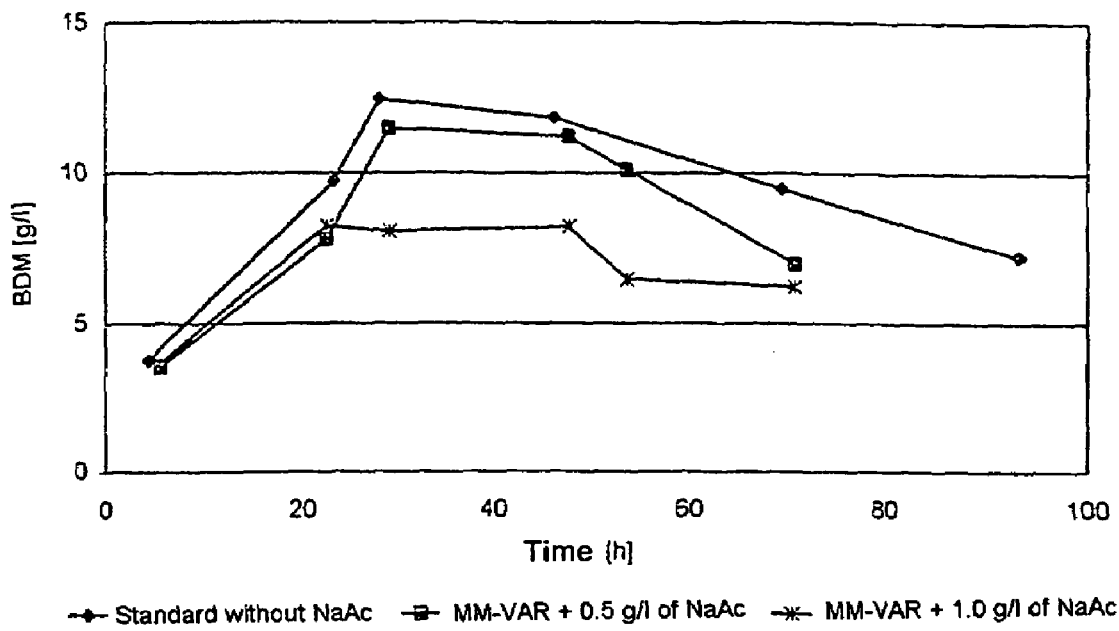
Figure 7  Course of the BDM on addition of NaAc to MM-VAR basal medium
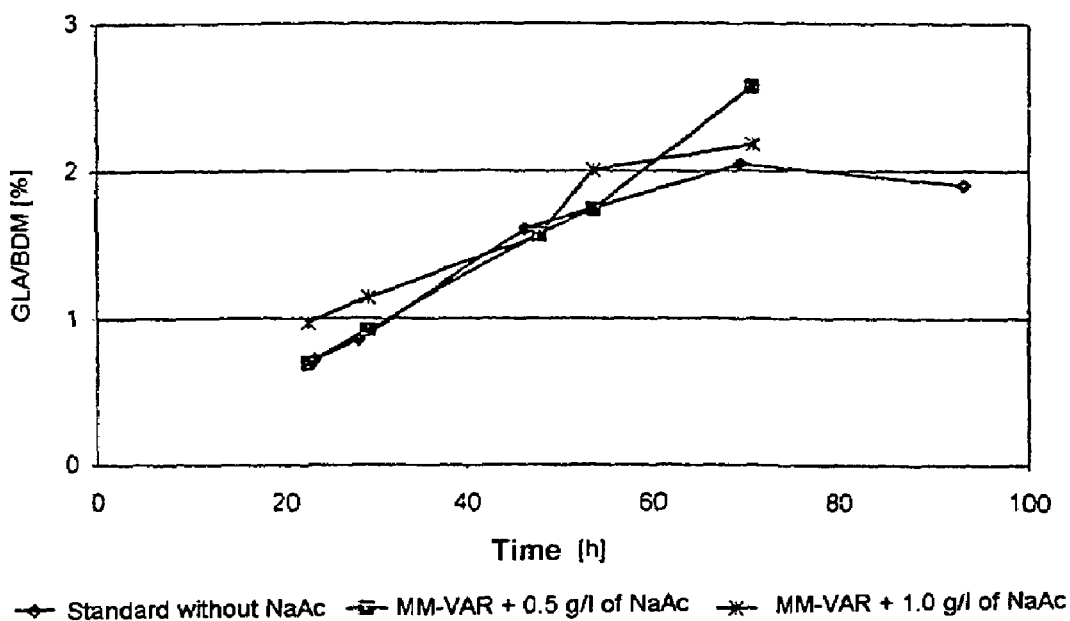
Figure 8  GLA content of the BDM on addition of NaAc to MM-VAR basal medium

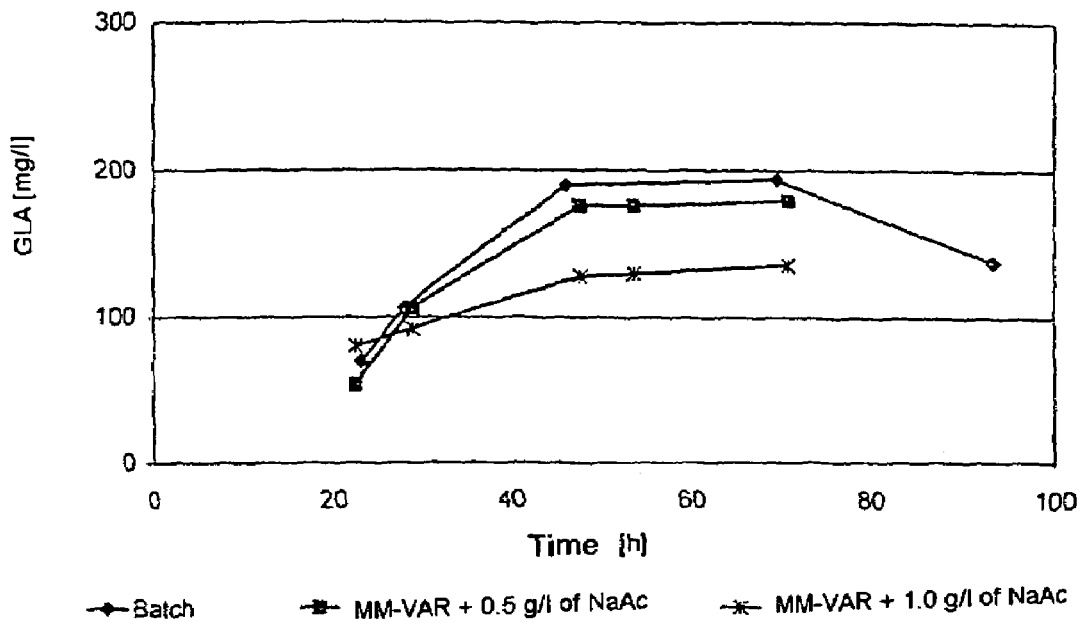
Figure 9   GLA concentration of the culture on addition of NaAc to MM-VAR basal medium
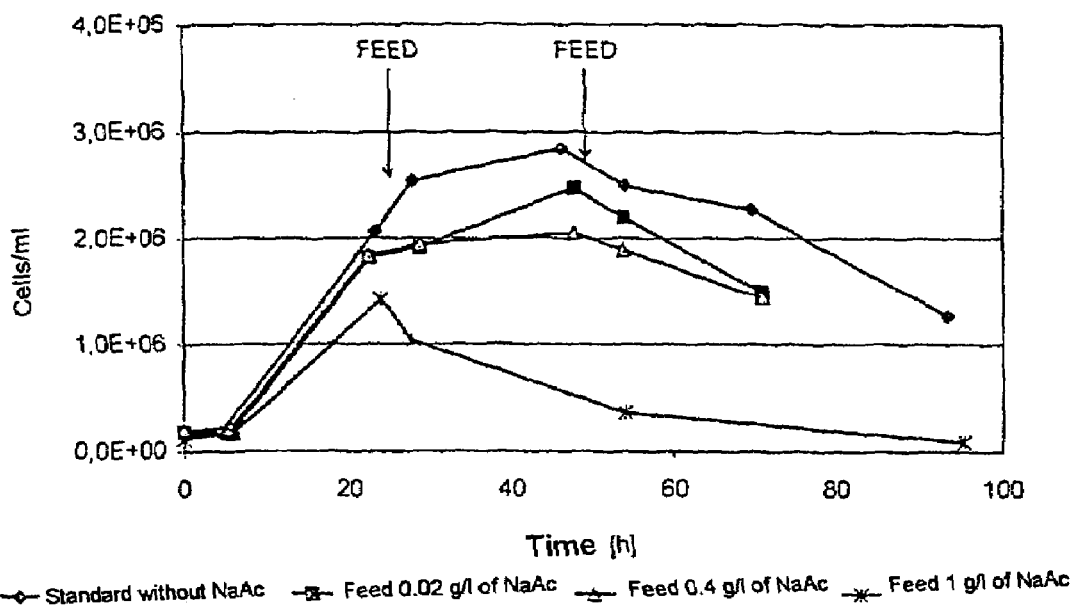
Figure 10   Course of the cell count on feeding NaAc during culturing (t = 25 h, 54 h); the arrows indicate the time point of addition

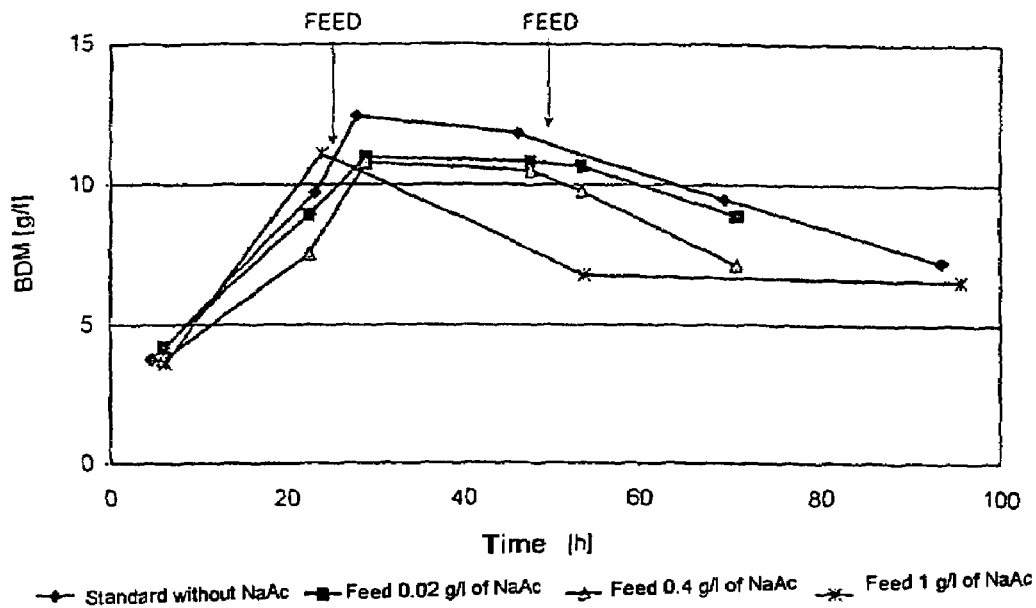
Figure 11  Course of the BDM on feeding NaAc during culturing (t = 25 h, 54 the arrows indicate the time point of addition
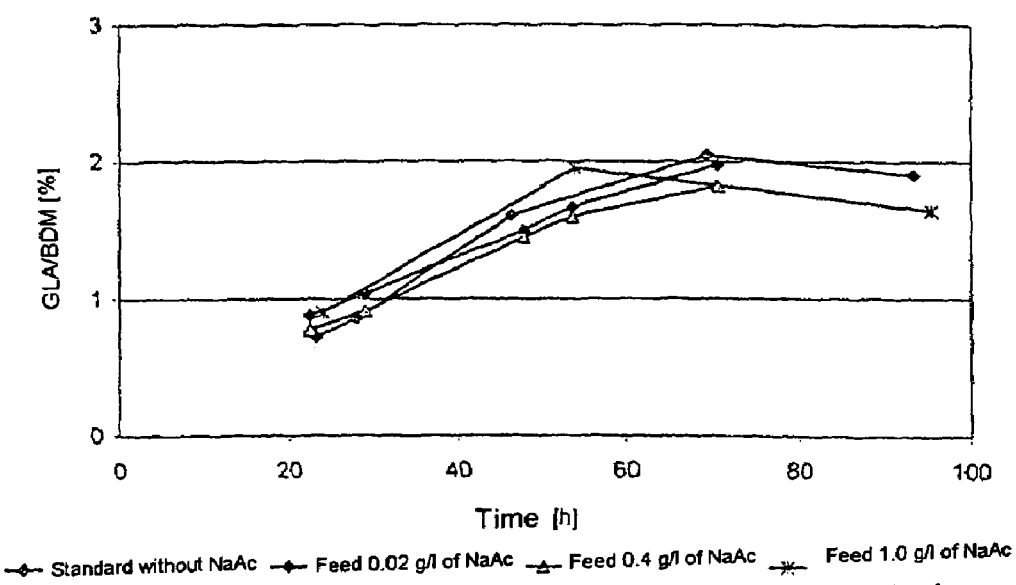
Figure 12  GLA content of the BDM on feeding NaAc during culturing (t = 25 h, 54 h)

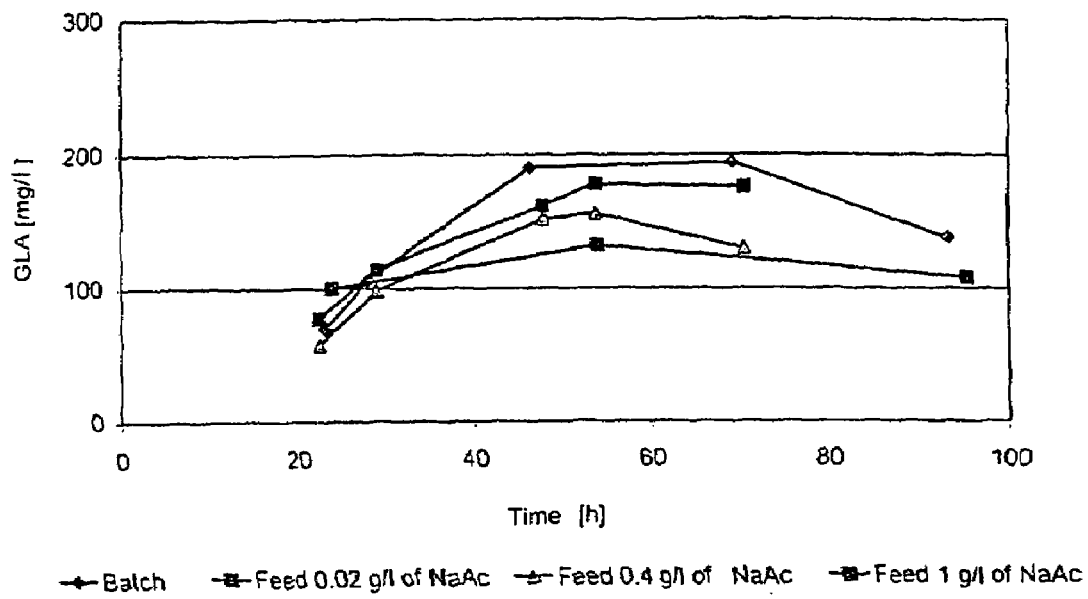
Figure 13 GLA concentration of the culture on feeding NaAc during culturing (t = 25 h, 54 h)
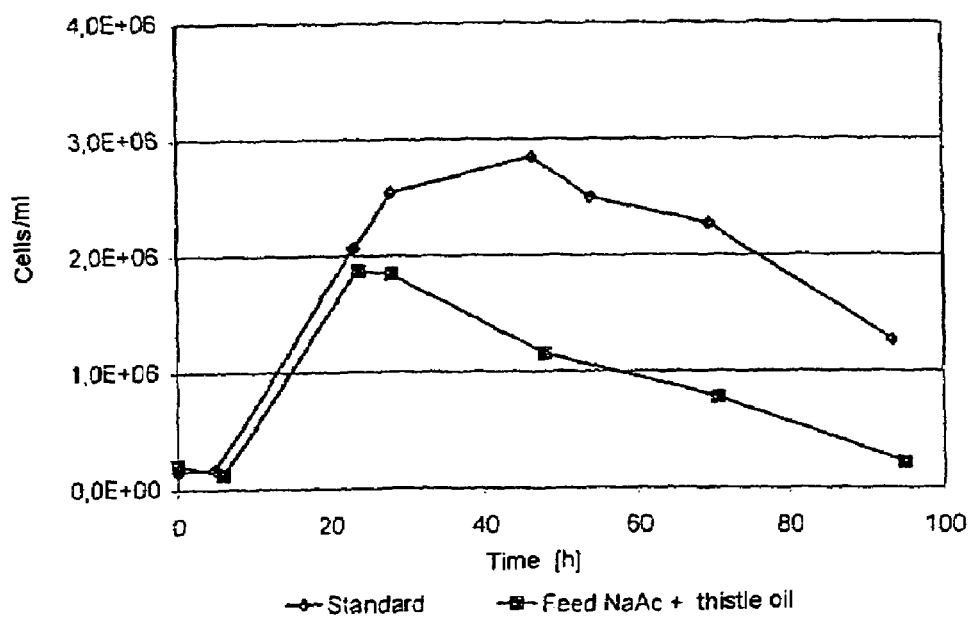
Figure 14 Effect of 0.5 g/l NaAc and 0.1% thistle oil on the cell count of *T. thermophila* B1868VII

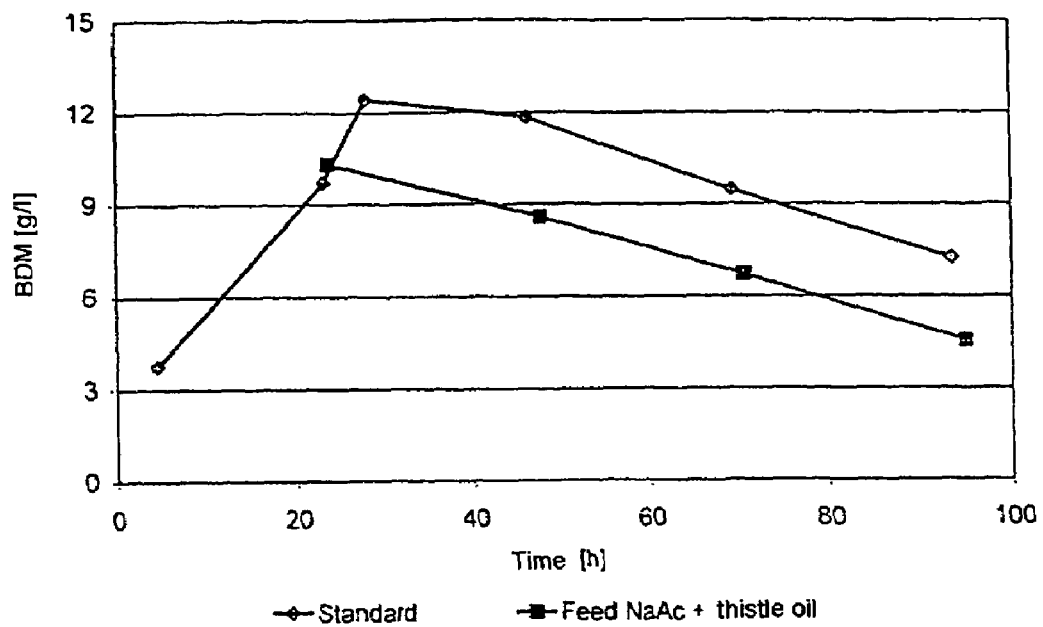
Figure 15 Effect of 0.5 g/l NaAc and 0.1% thistle oil on the BDM of *T. thermophila* B1868VII
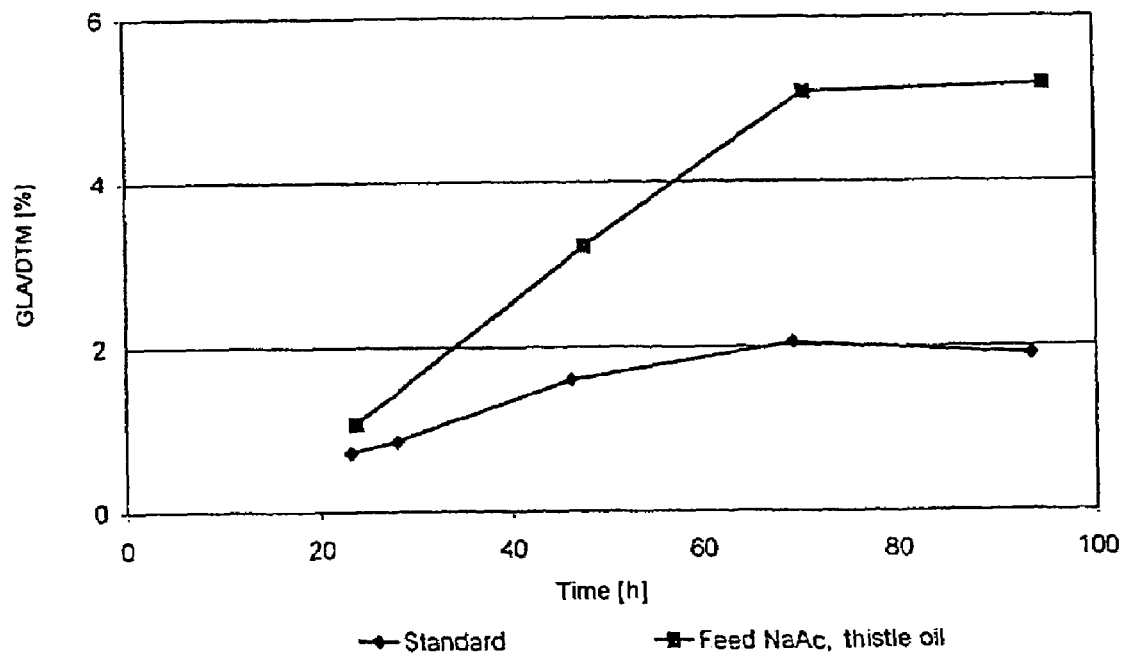
Figure 16 Course of the GLA content of T. thermophila B1868VII for growth on 0.5 g/l NaAc and 0.1% thistle oil

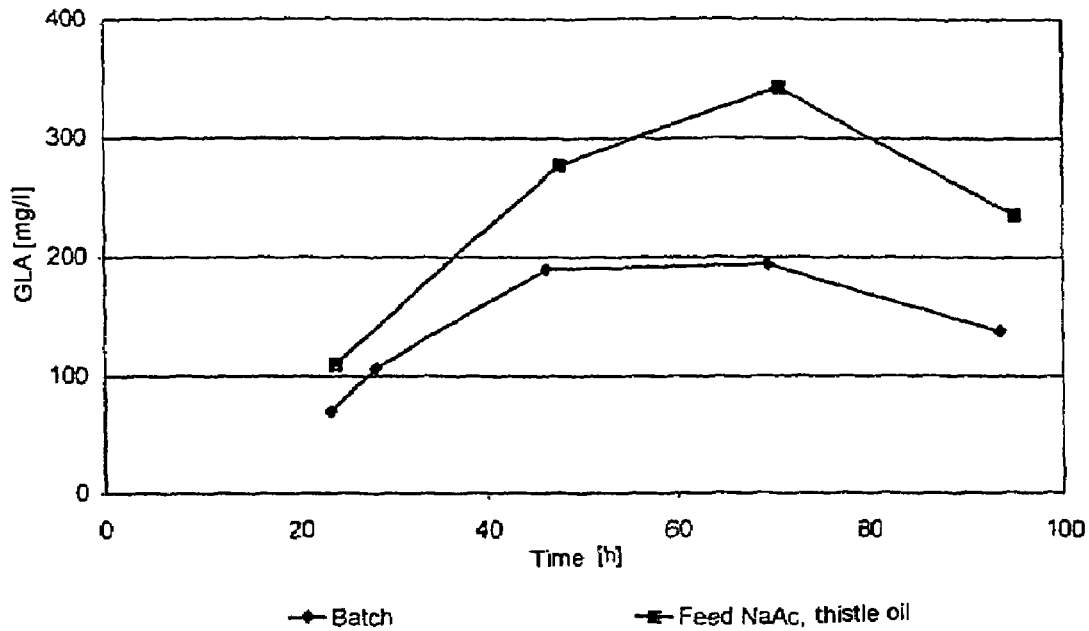
Figure 17 Effect of 0.5 g/l NaAc and 0.1% thistle oil on the GLA yield during culturing of *T. thermophila* B1868VII
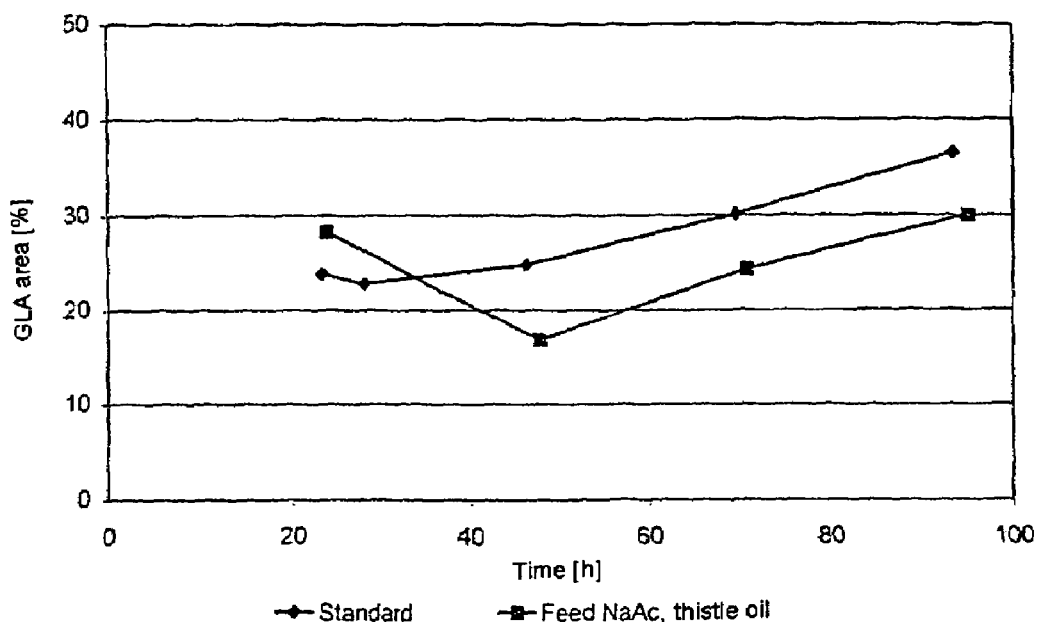
Figure 18 Course of the GLA area in the BDM of *T. thermophila* B1868VII for growth on 0.5 g/l NaAc and 0.1% thistle oil

METHOD FOR PRODUCING γ-LINOLENIC ACIDS FROM A CILIATE CULTURE BY ADDING SUITABLE PRECURSOR MOLECULES TO SAID CULTURE MEDIUM

The invention relates to a method for producing by fermentation omega-6-fatty acids (PUFA, polyunsaturated fatty acids), in particular γ-linolenic acid (GLA) in ciliates. The lipids/fatty acids can be used in human/animal nutrition, and also in the pharmaceutical sector.

The ciliates from which the lipids/fatty acids are obtained are preferably *Tetrahymena* sp. and particularly preferably *Tetrahymena thermophila*.

FIG. 1 shows a general diagram of the biosynthesis of PUFAs taking into account the enzymes involved in eukaryotes (modified in accordance with Gill & Valivety, Trends Biotechnol. 1997, 15:401–409). The conversion of steric acid (18:0) to oleic acid (18:1Δ9) is catalyzed by a delta 9-desaturase. Oleic acid is converted by a delta 12-desaturase into linoleic acid (18:2 Δ9,12; abbreviation LA), which in turn is converted by a delta 6-desaturase to γ-linolenic acid (18:3, Δ6,9,12; abbreviation: GLA), or by a delta 15-desaturase to α-linolenic acid (18:3 Δ9,12,15; abbreviation: ALA). The elongation of fatty acids is catalyzed by elongases, which, for example from γ-linolenic acid, form dihomo-γ-linolenic acid (20:3 Δ8,11,15; abbreviation: DGLA), which in turn is converted by a delta 5-desaturase to arachidonic acid (20:4 Δ5,8,11,15; abbreviation: ARA), a direct precursor molecule of physiologically active eicosanoids, for example prostaglandins, prostacyclins, thromboxanes, leukotrienes. In the formation of PUFAs which are derived from GLA (termed delta 6-unsaturated fatty acids hereinafter), it has been found that the conversion of LA to GLA by the delta 6-desaturase is the limiting step (Huang Y S & Mills D E, γ-linolenic acid: Metabolism and its role in nutrition and medicine. AOCS Press, Champaign, Ill., 1996).

Since vertebrates cannot introduce double bonds behind position 9 in fatty acids, unsaturated fatty acids such as LA and ALA are essential nutrients which cannot be synthesized by vertebrates and principally originate from plant sources in the diet. Mammals can convert LA by means of a delta 6-desaturase into GLA, which is an ARA precursor and also an essential precursor molecule of most prostaglandins. The formation of stearidonic acid (18:4 Δ6,9,12,15), a precursor molecule of the EPA, from ALA is likewise catalyzed by means of a delta 6-desaturase. The delta 6-desaturase is thus the first essential step in the biosynthesis of eicosanoids.

It has been found that the activity of delta 6-desaturase in mammals is impaired by factors such as, for example, alcohol consumption, stress, dietary deficiency and aging processes (Huang & Mills, 1996; Horrobin (1990) Rev. Contempt. Pharmacother. 1:1–45; Bolton-Smith C et al. (1997) Eur. J. Clin. Nutr. 51:619–624; Leventhal L J et al. (1993) Ann. Intern. Med. 119:867–873). This leads to deficient supply of GLA and thus ultimately to a deficiency of the GLA-derived molecules such as ARA and the physiologically important eicosanoids formed therefrom (Brenner R R (1976) Adv. Exp. Med. Biol. 83:85–101; Nakahara T et al. (1993) J. Jpn. Oil Chem. Soc. 42:242–253; Chapkin, R S (1998) Reappraisal of the essential fatty acids. In: Fatty acids in food and their health implications, $2^{nd}$ ed. (Chow C K, ed) Marcel Dekker, New York, N.Y.). Supplying GLA can not only compensate for a reduced endogenous level of delta-6 unsaturated fatty acids, but also can cover an increased requirement of these fatty acids (Horrobin (1990)). Therefore, consuming GLA via the diet is advantageous for biosynthesizing GLA-derived molecules (Fan. Y Y & Chapkin, R S (1998) J. Nutr. 128:1411–1414).

The finding that GLA has a variety of beneficial effects on the human body has in the meantime been reinforced by a multiplicity of scientific studies. Thus the beneficial action of GLA on, for example, atopic eczema, rheumatic arthritis, atheriosclerosis, diabetic neuropathy, migraines, schizophrenia and cancer has been demonstrated by clinical studies. In these studies, not only a statistically significant improvement, but also a clinically significant improvement, in the clinical picture was targeted.

Owing to these beneficial characteristics, there is a broad spectrum of use for GLA in the pharmaceutical, cosmetics, animal feed and food industry.

Most PUFAs from humans and animals either originate directly from the diet or via conversion of the essential fatty acids supplied via the diet by desaturaters and elongaters.

Only a few of the commercially utilized oil seeds produce GLA. GLA occurs only in the seed of various plants such as evening primrose (*Oenothera biennis*, approximately 10% GLA, based on the total fatty acid content), borage (*Borago officinalis*, approximately 23%) and blackcurrant (*Ribes nigrum*, approximately 18%). In addition, various microorganisms are also known as sources of GLA, for example the fungi Mucor and *Mortierella* (up to approximately 25%), the blue algae *Spirulina* (approximately 12–18%) and others. Particularly GLA-rich sources which have been described are ciliates, for example *Tetrahymena* (up to 47%; Hill, D L (1972) The biochemistry and physiology of *Tetrahymena*, Chapter 3, 46–73. Academic press, New York, London; Erwin, J & Bloch, K (1963) J. Biol. Chem. 238:1618–1624).

The production of GLA by fermentation from various fungi, for example *Mortierella* and *Mucor*, has already been described in the literature (Nakajima et al, Essent. Fatty Aicosanoids, Invited Pap. Int. Congr., $3^{rd}$, 1992, 57–64; Nakahara et al, Industrial appl. of single cell oils, AOCS Press, (1992), 61–97). A sufficient oxygen supply which is essential for GLA production may be implemented on an industrial scale only with great expenditure owing to the usually high viscosity of the culture medium in the case of fungi with filamentous growth, and this problem is still waiting to be overcome (Hiruta et al., j. Ferm. Biotech., (1997), 83, 79–86; Chmiel, Bioprozeβtechnik 2, (1991), 287–302; Crueger & crueger, Biotechnologie—Lehrbuch der angewandten Mikrobiologie [Biotechnology—textbook of applied microbiology], (1989), 224–266).

Commercial production of GLA from these natural sources is therefore burdened with serious disadvantages and problems which have to date impeded its use on an industrial scale. Not only the quality, but also the quantity, of the oils produced from these organisms varies and the oils have a very heterogeneous composition, which requires complex and expensive purification steps to enrich the GLA. Cultivating GLA-containing plants, furthermore, is not very economic (Hansen C E et al. (1991) J. Sci. Food Agric. 54:309–312). For the production of GLA-containing oils, it has been found that the space/time yield in some GLA-producing microorganisms is markedly better than is the case with higher plants.

For this reason, the production of GLA by fermentation by means of microorganisms offers a highly promising alternative to other GLA sources which have not been realized to date to a satisfactory extent, however.

The fatty acid spectrum of many microorganisms is less heterogeneous than with higher organisms, which offers advantages in purification. Furthermore, production by fermentation is not dependent on external factors such as weather, food supply, etc. Moreover, PUFAs prepared in this manner are substantially free from contaminants, which are due, for example, to environmental pollution. A further advantage is the reliable availability of the GLA produced by fermentation processes, in contrast to GLA from plant sources, for example.

Owing to the great interest in providing PUFAs or GLA industrially, there are copious methods in the prior art for optimizing production of these fatty acids by fermentation. Examples of these may be found in Ratledge C (1993) Trends Biochem. 11:278–284; Ratledge C (1989) Biochem. Soc. Trans. 17:1139–1141, Gosselin Y et al. (1989) Biotechnol. Lett. 11:423–426 and also the international patent application WO 86/03518). However, for production of GLA by fermentation by microorganisms on an industrial scale it is necessary to increase the GLA content, since the fermentation of PUFA-producing microorganisms is complex and expensive and is therefore uneconomic at the currently achievable GLA contents (supra Ratledge 1993). Furthermore, owing to the low GLA content based on the total lipids, purification is necessary, which cannot be carried out quantitatively, so that producing high-purity GLA by fermentation is currently not possible in significant yields from practical aspects.

On account of its GLA content, which is already naturally relatively high, particularly *Tetrahymena* could be suitable for producing GLA by fermentation. *Tetrahymena* can be cultivated in a fermenter and high cell densities can be achieved (Kiy, T. & Tiedtke (1992) Appl. Microbiol. Biotechnol. 37, 576–579; Kiy, T. & Tiedtke, A. (1992) Appl. Microbiol. Biotechnol. 38, 141–146).

PUFAs (including GLA) are present in *Tetrahymena* predominantly bound to phospholipids (PL) of the cell membranes. The cells contain 3.5 to 4 times more phospholipid than neutral lipid (storage lipids) (Lees et al, Biochemistry (1996) 5 (5), 1475–1481, Jonah et al., (1971) Biochimica et biophysica acta, 231, 80–92). However, the area of the cell membranes is limited, and in culture can only be increased by increasing the cell count. This places a natural limit to an increase in the PUFA content, since the cell count cannot be increased arbitrarily in culture.

The amount of neutral lipids (storage lipids) per cell can, in contrast, be increased and accumulated in the form of lipid droplets. This has been described for the targeted feed of acetate (Okuyama et al., J. Biol. Chem., (1977) 253 (10), 3588–3594; Borowitz et al., Biochim. et biophys. acta, (1976) 424, 114–124).

The proportion of GLA in the neutral lipids (NL) is, however, very low (6.7% (w/w) in the NL with 25.6% (w/w) in the total lipid (Jonah et al., Biochimica et biophysics acta, (1971) 231, 80–92), or 2.1% (w/w) in the NL with 29.5% (w/w) in the phospholipids (PL) and 19% (w/w) in the total lipid (Erwin et al. J. Biol. Chem., (1963) 238 (5), 1618–1624)). The composition of the fatty acids is not changed by supplying acetate (Holz et al., (1973), Biol *Tetrahymena*, 99–122).

For *Tetrahymena pyriformis*, an increase in cell count is reported when acetate is supplied (from $1.2 \times 10^5$ to $1.6 \times 10^5$ cells per ml when 0.1% acetate is added to a basal medium which does not contain glucose. With a basal medium which contains glucose the increase is not significant ($1.85 \times 10^5$ without, and $1.9 – 10^5$ cells per ml, with acetate) (Mavrides, (1973), Can. J. Biochem, 323–331, Medium composition: Dewey et al, (1950) Arch. Biochem. Biophys, 29, 281). The cell counts reported in these publications, however, are far below the cell counts which can be achieved using the media which can be used according to the invention (maximum $2 \times 10^5$ compared with $1 \times 10^6 – 3 \times 10^7$ in the medium used in the invention).

It is therefore an object of the present invention to provide a method for producing PUFAs, preferably GLA, by means of which markedly increased GLA yields can be achieved on an industrial scale. This method is to be technically simple, simple in handling, reliable and inexpensive.

It was a further object of the present invention to increase the GLA content in the neutral lipid in order to obtain the GLA in a purer form.

These objects, and also other objects which are not mentioned explicitly, but can be derived or inferred without problem from the context discussed herein at the outset are achieved by a method having all the features of patent claim 1. Expedient modifications of the inventive method are brought within the scope of protection in the subclaims which are referred back to claim 1.

This is due to the fact that by culturing ciliates under conditions known per se in the fermenter and adding GLA precursor molecules to the culture medium, an increased yield of GLA can be achieved in a manner which could not have been predicted.

Particularly preferably, in addition to the GLA precursor molecules, acetate is also added to the culture medium.

In a preferred embodiment of the present invention, the ciliate is *Tetrahymena* sp.

In a further preferred embodiment of the present invention, the ciliate is *Tetrahymena rostrata* (e.g. ATCC 30770).

In another further preferred embodiment of the present invention, the ciliate is *Tetrahymena pyriformis* (e.g. ATCC 30039, 30005, 30202).

In another further preferred embodiment of the present invention, the ciliate is *Tetrahymena thermophila* B1868 VII (e.g. ATCC 30384).

Preferably, the acetate is first added 20–39 hours after culturing is started, particularly preferably is first added after 25–35 hours.

In a further preferred embodiment of the present invention, the acetate is added in two stages.

Therefore, it is a particularly preferred embodiment of the present invention if a first feed pulse is added 20–39 hours after the start of culturing and a second feed pulse is added 40–70 hours after the start of culturing, particularly preferably a first feed pulse being added after 25–35 hours and a second feed pulse being added after 50–60 hours.

A further particularly preferred embodiment of the present invention is continuous addition of the acetate over the entire culturing period, the addition being started 20 hours after the start of culturing, particularly preferably 25 hours after the start of culturing, the acetate being added at a rate of at least 0.05 g/l per hour.

Preferably, the GLA precursor molecules are palmitic acid (C16:0), stearic acid (C18:0), oleic acid (C18:1) and/or linoleic acid (C18:2), or triglycerides, diglycerides, monoglycerides, phospholipids, esters or salts of the corresponding precursor molecules.

In a preferred embodiment of the present invention, the GLA precursor molecules are added to the culture in the form of natural oils such as sunflower seed oil.

In a further preferred embodiment of the present invention, the GLA precursor molecules are added to the culture in the form of the thistle oil.

In another further preferred embodiment of the present invention, the GLA precursor molecules are added to the culture in the form of olive oil.

The acetate is preferably added in the form of acetic acid or as a salt of acetic acid, for example as sodium acetate.

In studies of the abovementioned inventors which have led to the present invention, it was surprisingly found that an addition of acetate before inoculation, and also during culture, leads to poorer growth (Example 3). There was no marked change in either the fatty acid spectrum or the GLA content of the biomass, so that overall an impairment in GLA yield occurs.

In various feed experiments then carried out in which Tetrahymena was supplied with either only fatty acid precursors, only triacylglycerides of the precursor molecules, only acetates or a combination of triacyl glycerides of the precursor molecules and acetate, surprisingly it was found that combined supply of Tetrahymena sp. with said precursor molecules and with acetate brings about a particularly desirable increase not only of the neutral lipid content but also of the GLA content in the neutral lipids, which leads to an increase in the GLA content in the biomass DM by 250%, from 2.0% (w/w) to 5.0% (w/w). It was particularly surprising that addition of acetate staggered in time, about 20–40 hours after the start of the culturing, brings about particularly high yields of GLA. As a comparison, standard cultures were carried out without additions of fatty acid precursors and acetate.

According to the invention, therefore, ciliates are cultured under conditions under which they have a high PUFA content, preferably a high GLA content.

For the purposes of the present invention, a high PUFA content or GLA content is taken to mean that the corresponding fatty acids are present in the cell and/or the culture broth in the form of free fatty acids, as phospholipid, as neutral lipid or else in other forms in which fatty acids can occur under usual biological conditions.

The methods by which the γ-linolenic-acid-containing lipid or the γ-linolenic acid can be isolated from the culture or the culture broth are familiar to those skilled in the art.

One method here can be, to isolate the γ-linolenic-acid-containing lipids from the ciliates, to carry out the following stages:
 (i) cooling the fermentation broth down to 0–10° C., then centrifuging or filtering the cooled culture broth,
 (ii) drying the resultant biomass,
 (iii) extracting the resultant lipids by
  (a) extracting the biomass DM (BDM) obtained from (ii) with a polar solvent, preferably ethanol, which can extract the total lipid,
  (b) instead extracting the neutral lipid from the BDM with a nonpolar solvent, preferably n-hexane, and/or
  (c) treating the total lipid obtained from (a) with a nonpolar solvent to separate the neutral lipids and polar lipids, e.g. the phospholipids.

A further method to isolate the free γ-linolenic acid or esters thereof from the ciliates could be to carry out the following stages:
 (i) Saponification or esterification of the products obtained in stages (ii) or (iii) of the above method to produce free fatty acids or esters
 (ii) Enriching the GLA by precipitation methods (e.g. urea precipitation) and/or chromatographic methods A further method to isolate the free γ-linolenic acid directly from the fermentation broth could comprise the following stages:
 (i) cooling down the fermentation broth to 0–10° C., then centrifuging or filtering (with subsequent dilution to ensure filterability)
 (ii) hydrolyzing the released lipids by endogenous tetrahymena lipases or by adding other lipases
 (iii) enriching the GLA by precipitation methods (e.g. urea precipitation) and/or chromatographic methods In addition, it is obvious for those skilled in the art to synthesize structural lipids (e.g. triglycerides, phospholipids) from the lipids, fatty acids or fatty esters obtained as shown above, for example.

It is clear that a multiplicity of similar purification methods are available to those skilled in the art, which methods can be modified in one or more of these stages without leaving the scope of the present invention. Even a completely different purification plan would not change anything here, since many different purification plans can be derived from the prior art, and a selected purification of this type corresponds to the usual knowledge of those skilled in the art.

The figures described hereinafter contribute to an improved understanding of the present invention.

FIG. 1 shows a general diagram of the biosynthesis of PUFAs in eukaryots

FIG. 2 shows the biomass dry matter achieved in g/l using MM-Var (standard medium), MM-Var+thistle oil and MM-Var+olive oil (two parallel trials each)

FIG. 3 shows the percent GLA by weight achieved based on the biomass dry matter in % using MM-Var (standard medium), MM-Var+thistle oil and MM-Var+olive oil (two parallel trials each)

FIG. 4 shows the GLA yield achieved in mg/l using MM-Var (standard medium), MM-Var+thistle oil and MM-Var+olive oil (two parallel trials each)

FIG. 5 shows the GLA yield achieved in area [%] in g/l using MM-Var (standard medium), MM-Var+thistle oil and MM-Var+olive oil (two parallel trials each). The area [%] show the GLA proportion of the total lipid content.

FIG. 6 shows the course of cell count on addition of NaAc to MM-Var basal medium FIG. 7 shows the course of biomass DM on addition of NaAc to MM-Var basal medium FIG. 8 shows the GLA content of the biomass DM on addition of NaAc to MM-Var basal medium FIG. 9 shows the GLA concentration of the culture on addition of NaAc to the MM-Var basal medium FIG. 10 shows the course of the cell count on feeding NaAc during culturing (t=25 h, 54 h); the arrows indicate the time point of addition FIG. 11 shows the course of the biomass DM on feeding NaAc during culturing (t=25 h, 54 h); the arrows indicate the time point of addition FIG. 12 shows the GLA content on feeding NaAc during culturing (t=25 h, 54 h)

FIG. 13 shows the GLA concentration of the culture on feeding NaAc during culturing (t=25 h, 54 h)

FIG. 14 shows the effect of 0.5 g/l of NaAc and 0.1% thistle oil on the cell count of T. thermophila B1868VII.

FIG. 15 shows the effect of 0.5 g/l of NaAc and 0.1% thistle oil on the biomass DM of T. thermophila B1868VII.

FIG. 16 shows the course of the GLA content of T. thermophila B1868VII with growth on 0.5 g/l of NaAc and 0.1% of thistle oil FIG. 17 shows the effect of 0.5 g/l of NaAc and 0.1% thistle oil on the GLA yield during culturing of T. thermophila B1868VII.

FIG. 18 shows the course of the GLA area in biomass DM of T. thermophila B1868VII with growth on 0.5 g/l of NaAc and 0.1% thistle oil.

In view of the details set forth above, it is clear to those skilled in the art that similarly good GLA yields can be achieved using the inventive process with a multiplicity of other *Tetrahymena* sp., for example *T. silvana* (e.g. ATCC 50084), *T. malaccensis* (e.g. ATCC 50065), *T. asiatica* (e.g. ATCC 50068), *T. borealis* (e.g. ATCC 30203), *T. canadensis* (e.g. ATCC 50098), *T. australis* (e.g. ATCC 30349), *T. vorax* (e.g. ATCC 30421), *T. furgasoni* (e.g. ATCC 9357), *T. setosa* (e.g. ATCC 30782) and *T. tropicalis* (e.g. ATCC 30275).

The examples set forth hereinafter describe the invention in more detail. However, the examples are not to be considered limiting. If not otherwise specified, *Tetrahymena thermophila* B1868VII (e.g. ATCC 30384) was used for the individual experiments.

EXAMPLE 1

Standard Culture 20 ml of MM-Var medium (see Table 1) were charged into 100 ml conical flasks, or 100 ml of MM-Var medium were charged into 500 ml conical flasks with baffles, closed with a cellulose/cotton stopper and sterilized for 20 min at 121° C.

If appropriate, before the sterilization, further additives were placed in the medium.

TABLE 1

| Composition of MM-Var medium | |
|---|---|
| Substrate | Concentration |
| Skimmed milk extract | 2% |
| Glucose | 1% |
| Yeast extract | 0.5% |
| Na—Fe-EDTA | 0.003 |
| Constituents are dissolved in tap water | |

Preliminary Cultures

For the preliminary cultures, 100 ml flasks containing 20 ml of medium were inoculated with MM-Var medium (see Table 1) of a cell density of approximately $5 \times 10^4 – 1 \times 10^5$ cells per ml and cultured over 2 days at 25° C., 60 rpm. The cell count reached a value between $1 \times 10^6$ and $3 \times 10^6$ cells per ml.

Main Cultures in Shake Flasks

The shake flask experiments were carried out in 500 ml conical flasks containing 100 ml of medium. The experimental flasks were inoculated with a cell density of approximately $5 \times 10^4 – 1 \times 10^5$ per ml and cultured over 2 days at 25° C., 100 rpm.

Fermentations on a 1 l or 5 l Scale

Fermentations were carried out in a 1 l fermenter (700 ml working volume), 5 l fermenter (3 l working volume) and a 13 l fermenter (10 l working volume). The fermenters were equipped as standard with a pH electrode, a pO$_2$ electrode, an aeration ring, a stirrer shaft with disk vein agitator, feed line for acid/alkali, feed line for feeding, inoculation fittings and sampling.

The fermenters were charged with the working volume of medium and sterilized in a sterilizer for half an hour at 123° C.

Fermentation conditions were as specified in Table 2.

TABLE 2

| Process parameters | |
|---|---|
| Parameter | Value |
| Aeration rate | 1 vvm |
| pH | 7, regulated with acid (for example phosphoric acid) and base (for example NaOH) |
| Agitator tip speed | Linear increase from 0.3 m/s to 1.2 m/s in the first 24 hours |
| Temperature | 28° C. |
| Inoculation density | $5 \times 10^4 – 1 \times 10^5$ cells per ml |

The fermentations were inoculated with a main culture from a shake culture (see above).

Biomass Determination

To determine the biomass dry matter, 5 ml of cell culture were centrifuged for 10 min at 3400 g and 4° C., the supernatant was decanted and the cell pellet was frozen at −80° C. The frozen biomass was lyophilized and the weight of the biomass dry matter was determined.

Cell Count Determination

The cell density was determined using the CASY 1 Cell Counter+Analyser System, Model TTC, Schärfe System. For measurement, the cells were diluted (1:500) in a weak CASY electrolyte solution and transported through a capillary of 150 μm diameter. The cells in a range of 15–50 μm particle size were counted.

Determination of Neutral Lipid Content in Biomass Dry Matter

The nonpolar lipid constituents (neutral lipids) were extracted from the biomass dry matter with n-hexane. For one batch, approximately 500 mg of biomass dry matter were stirred in 5 ml of n-hexane for 1 h at 60° C., then centrifuged for 2 min at 2700 g and the supernatant was purified by filtering off suspended matter. For the filtration, a Pasteur Pipette filled with cotton wool was used, having a fill height of approximately 1 cm. The cell residue for the first extraction was extracted a further time with 5 ml of solvent, the biomass was centrifuged off and the supernatant filtered. The purified organic phases of the two extractions were combined, the solvent was completely evaporated on a rotary evaporator and the amount of extracted lipid was determined by weighing.

Qualitative and Quantitative Analysis of Extracted Lipids

Extracted lipids were analyzed qualitatively and quantitatively using a Iatroscan™ new MK-5 Analyser. The chromatography material used was separating rods (chromarods) using thermally resistant silica gel as surface material. The rods were stored in a desiccator and, before each separation operation, were calcined to remove interfering substances. The measurement conditions of the FID were chosen to be: scan rate 30 s/scan, O$_2$ flow rate 2 l/min and H$_2$ flow rate 160 ml/min.

The lipid to be analyzed was dissolved in chloroform/methanol (2:1) at a concentration of approximately 10 g/l and 1 μl thereof was applied to a separation rod. Separation was carried out over a period of 30 min in a mobile phase whose composition is specified in Table 3.

TABLE 3

Mobile phase for the Iatroscan analysis of lipids

| Mobile phase | Composition | Ratio (v/v) |
|---|---|---|
| For separating neutral lipids | n-hexane, chloroform, isopropanol, formate, acetate | 800:160:10:1:10 |

After the run, the rods were dried for 5 min at 80° C. and analyzed in the Iatroscan. Lipids were assigned and quantified by comparison with authentic standards. The standard solution was a mixture of 4.65 g/l of tripalmitic acid, 5.17 g/l of dipalmitic acid and 5.64 g/l of palmitic acid dissolved in methanol/chloroform (2:1). To establish calibration lines, the solution was applied to the separation rods in amounts of 0.5–2.0 µl, developed in solvent and analyzed by TLC-FID (Table 4).

TABLE 4

Quantification of fatty acids on the basis of results of GC analysis

| Reported result | Definition | Abbreviation | Unit |
|---|---|---|---|
| Area % | Relative content of an FA in total fatty acids | FA/TFA | area % |
| % by mass (w/w) | Absolute content of an FA in NL or in biomass DM (calculated via ISTD) | FA/NL, FA/BDM | % |

Determination of GLA Content by Means of Gas Chromatography (GC)

The fatty acid spectrum was determined by means of a gas chromatograph (HP GC 6890) equipped with a flame ionization detector (Hewlett-Packard Company, Wilmington, USA). The column used was an FFAP (Free Fatty Acid Phase) Permbond (Macherey & Nagel GmbH, Düren). The fatty acids were identified by comparison with the retention times of fatty acid methyl ester standards. On the basis of the known concentration of the standard, the concentration of fatty acids in the samples could be determined.

30–70 mg of the lyophilized biomass dry matter (see determination of biomass) were weighed out and were admixed with 1 ml of 20% strength methanolic HCl and 1 ml of methanolic standard solution (1 mg/ml). To liberate the fatty acids and transesterify them into fatty acid methyl esters, the samples were stirred in a closed test tube for two hours at 60° C. in a water bath and cooled to room temperature. To neutralize the sample, 1 ml of aqueous saturated sodium hydrogen carbonate solution was then added and the sample was mixed carefully. The fatty acid methyl esters were extracted by adding n-hexane. The batch was then mixed vigorously and phase separation was achieved by centrifuging for 2 min at 4300 rpm. About ⅔ of the upper organic phase was taken off and 1 µl of the sample was injected onto the GC column and analyzed (see also Table 5).

TABLE 5

Measurement conditions for the HP 6890 gas chromatograph

| | |
|---|---|
| Carrier gas: helium | 1.0 ml/min |
| Make up: helium | 20 ml/min |
| Injector temperature: | 255° C. |
| Split ratio | 10:1 |
| Injection volume | 1 µl |
| Detector temperature: | 255° C. |
| FID fuel gases | Hydrogen (30 ml/min), oxygen (300 ml/min) |
| Temperature profile | 160° C., 12 min–10° C./min to 230° C.–230° C., 5 min |

EXAMPLE 2

Effect of Thistle Oil (Linoleic Acid Source) on GLA Production 1 ml/l of thistle oil was added before sterilization to each of two 500 ml flasks containing 100 ml of MM-Var medium. The reference used was two 500 ml flasks containing 100 ml MM-Var medium. The thistle oil had the composition reported in Table 6. The fatty acids were in the form of triglycerides.

The results are shown in FIGS. 2 to 4. The addition increased the biomass from approximately 8.3 g/l to approximately 9.5 g/l (FIG. 2). The GLA content in the biomass content was increased only slightly (FIG. 3), but the higher biomass concentration increased the GLA concentration by volume by 28% (from 180 mg/l to 230 mg/l). Adding the thistle oil decreased the proportion of GLA in the total fatty acids from 33% to 22% (FIG. 5).

TABLE 6

Typical fatty acid contents of various natural raw materials

| Natural substance | Steric acid | Oleic acid | Linoleic acid | γ-linolenic acid |
|---|---|---|---|---|
| Thistle oil/safflower oil | 2.5% | 12.5% | 78.2% | |
| Evening primrose oil | 2% | 8.8% | 73.8% | 8.3 |
| Olive oil | 2.5% | 75.5% | 8.4% | |
| Sunflower seed oil | 4% | 25% | 65% | |

EXAMPLE 3

Effect of Olive Oil (Oleic Acid Source) on GLA Production

Before sterilization, 1 ml/l of olive oil was added to each of two 500 ml flasks containing 100 ml of MM-Var medium. Two 500 ml flasks containing 100 ml of MM-Var medium acted as reference. The olive oil had the composition given in Table 6 (above). The fatty acids were in the form of triglycerides. The results are shown in FIGS. 2 to 4. The addition increased the biomass from approximately 8.3 g/l to approximately 9.1 g/l (FIG. 2). The GLA content in the biomass was increased significantly (from 2.1% to 3%) (FIG. 3) and, together with the higher biomass concentration, the GLA concentration by volume was increased by 53% (from 180 mg/l to 275 mg/l). Adding the olive oil reduced the proportion of GLA in the total fatty acids from 33% to 24% (FIG. 5).

EXAMPLE 4

Effect of Acetate on GLA Production (Acetate in Basal Medium)

The fermentations were carried out in a 1-l fermenter containing 700 ml of MM-Var medium. One fermentation acted as reference, to the other two, 0.5 and 1.0 g/l of sodium acetate (NaAc) were added to the culture medium before sterilization.

Sodium acetate adversely affected cell growth of *tetrahymena thermophila* B1868VII during culturing (FIGS. 6 and 7). Not only cell density, but also biomass dry matter (BDM) of the experiments were below the results of the reference fermentation. Then as a direct correlation between amount of sodium acetate used and the inhibitory action on cell growth. The GLA content of the biomass dry matter was not altered by adding NaAc (FIG. 8).

Neutral lipids synthesis was also only altered slightly by adding sodium acetate (see Table 7).

TABLE 1

Lipid content on addition of NaAc to the basal medium

| Fermentation | NL/BDM [%(w/w)] | | GLA/NL [%(w/w)] | | GLA/NL [Area %] | |
|---|---|---|---|---|---|---|
| | 46 h | 70 h | 46 h | 70 h | 46 h | 70 h |
| Standard without NaAc | 8 | 11 | 8 | 10 | 17 | 26 |
| MM-VAR containing 0.5 g/l of NaAc | 8 | 17 | 10 | 12 | 18 | 22 |
| MM-VAR containing 1.0 g/l of NaAc | 11 | 17 | 8 | 14 | 16 | 26 |

After a culture time of 46 h, there was still no significant difference observable from the standard fermentation. An increase was not observed until after 70 h: adding NaAc to the MM-Var basal medium led to an increase in NL content from 11% to 17% (w/w). The GLA content in the neutral lipid showed only slight differences from the standard fermentation.

Surprisingly, adding NaAc decreased formation of GLA product by volume (FIG. 9).

EXAMPLE 5

Effect of Acetate on GLA Production (Acetate Added to Culture After 24 Hours)

The fermentations were carried out in a 1-l fermenter containing 700 ml of MM-Var medium. One fermentation acted as reference, to the others were added 0.2, 0.5 and 1.0 g/l of sodium acetate (NaAc) in the form of a sterilized (20 min at 121° C.), 10% strength solution added to the $29^{th}$ hour of fermentation. In the case of the fermentations to which 0.2 and 0.5 g/l of NaAc had been supplied at the $29^{th}$ hour, the same amount was added again at the $54^{th}$ hour of fermentation.

In the culturings, sodium acetate had an adverse effect on the cell growth of *Tetrahymena thermophila* B1868VII (FIGS. 10 and 11). Not only the cell density, but also the BDM of the experiments was below the results of the reference fermentation. There was a direct correlation between the amount of sodium acetate used and the inhibitory activity on the cell growth. When NaAc is fed during culturing, the direct reaction which may be observed is decreased growth or lowering of cell density. The GLA content of the biomass dry matter was unchanged by adding NaAc (FIG. 12).

Neutral lipid synthesis was also changed only slightly by adding sodium acetate (see Table 8).

TABLE 2

Lipid content on feeding NaAc

| Fermentation | NL/BDM [%(w/w)] | | GLA/NL [%(w/w)] | | GLA/NL[area %] | |
|---|---|---|---|---|---|---|
| | 46 h | 70 h | 46 h | 70 h | 46 h | 70 h |
| Standard without NaAc | 8 | 11 | 8 | 10 | 17 | 26 |
| Feed 0.02 g/l of NaAc | 8 | 12 | 8 | 14 | 15 | 26 |
| Feed 0.4 g/l of NaAc | 9 | 13 | 7 | 11 | 15 | 20 |

After a culture time of 46 h of acetate medium, no difference from the standard fermentation was observed. Even after 70 h, no significant increase was observed. The formation of GLA product by volume was impaired by adding acetate (FIG. 13).

EXAMPLE 6

Feeding Sodium Acetate and Thistle Oil

The fermentations were carried out in a 1 l fermenter containing 700 ml of MM-Var medium. One fermentation served as reference, to one 0.5 g/l of NaAc and 1 ml/l of thistle oil were added before sterilization, and to one 0.5 g/l of NaAc and 1 ml/l of thistle oil were added towards the end of the exponential phase (to the $28^{th}$ hour).

FIG. 14 and FIG. 15 show the course of the cell count and biomass dry matter. It may be seen that adding NaAc and thistle oil to the culture medium led to decreased growth of *Tetrahymena*. When substrate was added at the start of fermentation, compared with the reference fermentation, delayed exponential growth phase was observed; the BDM achieved was approximately the same. Addition after 28 h led to a decrease in the BDM as a result of the feed.

In FIG. 16, the GLA content per biomass is plotted during the course of fermentation. Culturing on thistle oil and sodium acetate caused a pronounced increase in the GLA content to 5.2% (w/w). The standard fermentation showed markedly low values of 2–3% (w/w). The increased GLA content, despite a decreased BDM, was expressed in a high GLA concentration of 342 mg/l (71 h; FIG. 17) having a GLA purity of 30 area % (FIG. 18).

EXAMPLE 7

Combined Feed of Olive Oil and Acetate

Similarly good results were also obtained by using olive oil.

The invention claimed is:

1. A process for producing omega-6-fatty acids by fermentation, characterized in that dilates are cultured in a culture medium to which γ-linolenic acid precursor molecules and acetate are added and in which the γ-linolenic acid is isolated from the ciliates after the culture is terminated, and wherein the acetate is added 20–39 hours after the start of the culture.

2. The process as claimed in claim 1, characterized in that *Tetrahymena* sp. is used.

3. The process as claimed in claim 2, characterized in that *Tetrahymena thermophila* is used.

4. The process as claimed in claim 2, characterized in that *Tetrahymena pyriformis* is used.

5. The process as claimed in claim 2, characterized in that *Tetrahymena rostrata* is used.

6. The process as claimed in claim 1, characterized in that the acetate is added in two stages, the first addition being performed 20–39 hours after the start of the culture and a second addition being performed 40–70 hours after the start of the culture.

7. The process as claimed in claim 1, characterized in that the acetate is added in two stages, a first addition being performed 25–35 hours after the start of the culture, and a second addition being performed 50–60 hours after the start of the culture.

8. The process as claimed in claim 1, characterized in that acetate is added continuously at a rate of 0.05 g/l per hour from the $20^{th}$ hour after the start of the culturing.

9. The process as claimed in claim 1, characterized in that the γ-linolenic acid precursor molecules are added in the form of palmitic acid (C16:0), stearic acid (C18:0), oleic acid (C18:1) and/or linoleic acid (C18:2), or in the form of triglycerides, diglycerides, monoglycerides, phospholipids, esters or salts of the corresponding fatty acid precursors.

10. The process as claimed in claim 1, characterized in that the acetate is added to the culture in the form of acetic acid or as a salt of acetic acid.

11. The process as claimed in claim 1, characterized in that the γ-linolenic acid precursor molecules are added in the form of natural oils, and the oil is added to the medium at a final concentration of 0.1 ml/l to 10 ml/l.

12. The process as claimed in claim 1, characterized in that the acetate is added as sodium acetate at a concentration of 0.1 g/l to 1 g/l.

13. The process as claimed in claim 1, characterized in that the GLA content of the biomass dry matter from the culture is at least 4% (w/w).

14. The process as claimed in claim 1, characterized in that the γ-linolenic acid concentration in the culture is at least 300 mg/l.

* * * * *

UNITED STATES PATENT AND TRADEMARK OFFICE
CERTIFICATE OF CORRECTION

| | | |
|---|---|---|
| PATENT NO. | : 7,081,356 B2 | Page 1 of 1 |
| APPLICATION NO. | : 10/468259 | |
| DATED | : July 25, 2006 | |
| INVENTOR(S) | : Anton Van V. Putten et al. | |

It is certified that error appears in the above-identified patent and that said Letters Patent is hereby corrected as shown below:

In Claim 1, at column 12, line 58, "mentation, characterized in that dilates are cultured in a" should read -- mentation, characterized in that ciliates are cultured in a --

Signed and Sealed this

Twenty-third Day of January, 2007

JON W. DUDAS
*Director of the United States Patent and Trademark Office*